(12) United States Patent
Frisbee

(10) Patent No.: US 7,100,227 B2
(45) Date of Patent: Sep. 5, 2006

(54) ANTI-SNORING PILLOW

(75) Inventor: Christine K. Frisbee, New York, NY (US)

(73) Assignee: First Impressions Home Marketing, Inc., New York, NY (US)

( * ) Notice: Subject to any disclaimer, the term of this patent is extended or adjusted under 35 U.S.C. 154(b) by 0 days.

(21) Appl. No.: 10/739,691

(22) Filed: Dec. 18, 2003

(65) Prior Publication Data

US 2004/0172760 A1    Sep. 9, 2004

Related U.S. Application Data

(63) Continuation-in-part of application No. 10/382,890, filed on Mar. 6, 2003, now abandoned.

(51) Int. Cl.
  *A47G 9/10* (2006.01)
  *A47C 20/00* (2006.01)

(52) U.S. Cl. ............................. 5/640; 5/655.9; 5/657; 5/490

(58) Field of Classification Search ................. 5/636, 5/637, 640, 644, 643, 645, 490, 655.9, 657, 5/482; D06/601
See application file for complete search history.

(56) References Cited

U.S. PATENT DOCUMENTS

| | | | |
|---|---|---|---|
| 1,349,072 A | 8/1920 | Lines | |
| 2,835,905 A | 5/1958 | Tomasson | |
| 2,940,088 A * | 6/1960 | Boos | ............................. 5/636 |
| 3,009,172 A | 11/1961 | Eidam | |
| 3,118,152 A | 1/1964 | Talley | |
| 3,312,987 A | 4/1967 | Emery | |
| 3,389,411 A | 6/1968 | Emery | |
| 3,648,308 A | 3/1972 | Greenawalt | |
| 4,118,813 A | 10/1978 | Armstrong | |
| 4,349,925 A | 9/1982 | Macomber | |
| 4,536,905 A | 8/1985 | DeSantis | |
| 4,660,238 A * | 4/1987 | Jay | ............................. 5/654 |
| 4,748,702 A | 6/1988 | Sandler | |
| 4,768,246 A | 9/1988 | Summer | |
| 4,768,248 A | 9/1988 | O'Sullivan | |
| D298,198 S | 10/1988 | O'Sullivan | |
| 4,780,921 A | 11/1988 | Lahn et al. | |
| 4,788,728 A | 12/1988 | Lake | |
| 4,803,743 A * | 2/1989 | Greenawalt | ..................... 5/636 |
| 4,847,931 A * | 7/1989 | Bard | ............................. 5/644 |
| 4,850,067 A | 7/1989 | Latorre | |
| D306,112 S | 2/1990 | Forsland | |
| 4,916,765 A | 4/1990 | Castronovo, Jr. | |
| 4,928,336 A | 5/1990 | Petillo, Sr. | |
| D308,311 S | 6/1990 | Forsland | |
| D310,610 S | 9/1990 | Dixon | |

(Continued)

OTHER PUBLICATIONS

Hermell Products, Inc.; Neck Pillows; 4 pages; http://www.hermell.com.

(Continued)

*Primary Examiner*—Michael Safavi
(74) *Attorney, Agent, or Firm*—Ohlandt, Greeley, Ruggiero & Perle, L.L.P.

(57) ABSTRACT

An anti-snoring pillow having a top pillow, a bottom pillow, and a covering is provided. The bottom pillow has a top surface angled with respect to a bottom surface. The top surface of the bottom pillow has a head-receiving cavity defined therein. The covering has a top section, a middle section, and a bottom section. The top pillow is in the top section and the bottom pillow is in the bottom section. The middle section maintains the top pillow centered over the head-receiving cavity during use.

5 Claims, 5 Drawing Sheets

U.S. PATENT DOCUMENTS

| | | | |
|---|---|---|---|
| 5,014,377 A | 5/1991 | Dixon | |
| 5,016,303 A | 5/1991 | Tanaka et al. | |
| 5,018,231 A | 5/1991 | Wang | |
| 5,025,518 A | 6/1991 | Summer | |
| 5,123,132 A | 6/1992 | Dixon | |
| 5,138,732 A * | 8/1992 | Wattie et al. | 5/636 |
| 5,369,829 A | 12/1994 | Jay | |
| D356,919 S | 4/1995 | Nadeau | |
| D359,189 S | 6/1995 | Righini | |
| 5,432,967 A | 7/1995 | Raftery | |
| 5,457,833 A | 10/1995 | Jay | |
| D370,821 S | 6/1996 | Mata | |
| 5,537,703 A | 7/1996 | Launder et al. | |
| D381,233 S | 7/1997 | Torbik | |
| D383,026 S | 9/1997 | Torbik | |
| 5,682,633 A | 11/1997 | Davis | |
| 5,689,844 A | 11/1997 | Liu | |
| 5,697,112 A * | 12/1997 | Colavito et al. | 5/657 |
| D388,649 S | 1/1998 | Chekuri | |
| D388,650 S | 1/1998 | Davis | |
| D389,691 S | 1/1998 | Benedict et al. | |
| 5,743,271 A | 4/1998 | Royo-Salvador | |
| 5,781,947 A | 7/1998 | Sramek | |
| 5,797,154 A | 8/1998 | Contreras | |
| D407,259 S | 3/1999 | Jackson | |
| 5,920,932 A | 7/1999 | Hershgordon | |
| 5,926,879 A | 7/1999 | Davis | |
| 5,926,880 A | 7/1999 | Sramek | |
| D413,752 S | 9/1999 | Denney | |
| D415,920 S | 11/1999 | Denney | |
| D416,428 S | 11/1999 | Jackson | |
| 6,006,380 A | 12/1999 | Sramek | |
| 6,026,330 A * | 2/2000 | Chuang | 607/100 |
| D439,100 S | 3/2001 | Owaku | |
| 6,202,233 B1 | 3/2001 | Achong | |
| 6,230,347 B1 * | 5/2001 | Alexander | 5/636 |
| 6,230,350 B1 | 5/2001 | Goldstein | |
| D444,980 S | 7/2001 | Mowat et al. | |
| 6,256,818 B1 * | 7/2001 | Hughes | 5/639 |
| D446,676 S | 8/2001 | Mayes | |
| 6,292,964 B1 * | 9/2001 | Rose et al. | 5/657 |
| 6,336,236 B1 * | 1/2002 | Dalton | 5/636 |
| 6,345,401 B1 | 2/2002 | Frydman | |
| 6,381,784 B1 | 5/2002 | Davis et al. | |
| 6,386,201 B1 | 5/2002 | Fard | |
| 6,446,288 B1 * | 9/2002 | Pi | 5/636 |
| 6,471,726 B1 | 10/2002 | Wang | |
| D466,750 S | 12/2002 | Landvik | |
| 6,490,743 B1 | 12/2002 | Adat et al. | |
| 6,523,199 B1 * | 2/2003 | Gross | 5/632 |
| D476,186 S | 6/2003 | Wang et al. | |
| 6,581,226 B1 | 6/2003 | Brustein | |
| 6,629,324 B1 | 10/2003 | Shapiro | |
| 6,701,555 B1 * | 3/2004 | Ermini | 5/644 |
| 2002/0112289 A1 | 8/2002 | Troop | |
| 2003/0000018 A1 | 1/2003 | Lanteri | |
| 2004/0019972 A1 * | 2/2004 | Schecter et al. | 5/645 |
| 2004/0068799 A1 * | 4/2004 | Wilson | 5/632 |

OTHER PUBLICATIONS

Foamex International, Inc. 2 pages; http://www.foamex.com/consumer/pillows.php.
Hidden Treasures 6 pgs; http://www.consumermedhelp.com/products.html.
Sealy Posturepedic "Snore Reduction Pillow", 3 pgs www.sealysnorereduction.com.
Comfort Trac "Contour Secret Pillow"; 3 pgs.
Federal Foam Technologies, Inc. 1 pg. http://www.federalfoam.com/products.htm.
JoAnnes Bed & Back; Pillows & Wedges; 2 pgs http://www.backfriendly.com.
Latex Pillows; 2 pgs http://www.allergybuyersclubshopping.com.
"Silent Night Stop Snoring Pillow", 2 pgs http://www.tvhaseverything.com.
"Pillow Positive" 5 pgs http://www.snorenet.net.

* cited by examiner

ANTI-SNORING PILLOW

CROSS REFERENCE TO RELATED APPLICATIONS

This application is a continuation-in-part of U.S. application Ser. No. 10/382,890 filed on Mar. 6, 2003, now abandoned, the contents of which are incorporated herein by reference.

BACKGROUND OF THE INVENTION

1. Field of the Invention

The present invention relates to a pillow, which addresses the problem of snoring in one's sleep. More particularly, the present invention relates to an anti-snoring pillow.

2. Description of Related Art

Typically, snoring while sleeping occurs in an individual who, due to his own physiology, is pre-disposed to snore upon the relaxation of various musculature around and about the individual's face and neck region, which in turn creates a set of conditions wherein a flap of tissue located in the individual's throat is caused to vibrate in synchronization with that individual's breathing.

Generally, snoring tends to occur in individuals while in deep sleep at which point in time the individual's facial musculature has relaxed to the extent that said individual's mouth is in at least a partially open position.

The occurrence of snoring in many individuals can become so pronounced as to cause considerable annoyance to that individual's bedmate, even to the extreme of causing loss of sleep to such a bedmate. The problems caused by a sleeping individual's pronounced snoring have also been known to result in serious relationship disruptions, which go well beyond the loss of sleep.

Consequently, the alleviation of snoring in a sleeping individual has been a long sought goal for many years.

SUMMARY OF THE INVENTION

An anti-snoring pillow having a top pillow, a bottom pillow, and a covering is provided. The bottom pillow has a top surface angled with respect to a bottom surface. The top surface of the bottom pillow has a head-receiving cavity defined therein. The covering has a top section, a middle section, and a bottom section. The top pillow is in the top section and the bottom pillow is in the bottom section. The middle section maintains the top pillow centered over the head-receiving cavity during use.

In another embodiment, the anti-snoring pillow has a top pillow, a bottom pillow, and a covering. The top pillow has a first density and the bottom pillow has a second higher density. The bottom pillow has a top surface configured to receive the top pillow and to position a head of a user in a predetermined position when in use. The covering has a top section, a middle section, and a bottom section. The top pillow is in the top section, while the bottom pillow is in the bottom section. The middle section maintains the top pillow in a selected position with respect to the bottom pillow during use.

The above-described and other features and advantages of the present invention will be appreciated and understood by those skilled in the art from the following detailed description, drawings, and appended claims.

DETAILED DESCRIPTION OF THE INVENTION

The present invention is directed to a pillow, which addresses the problem of snoring in one's sleep. More particularly, the present invention relates to an anti-snoring pillow, which embodies a combination of essential physical characteristics, which characteristics collectively serve to substantially reduce the incidence of snoring by the user of such pillow while sleeping. The pillow of the present invention allows the user to sleep in a normal position, without the use of any restrictive device, such as might otherwise be employed to prevent or alleviate snoring.

Figure 1:
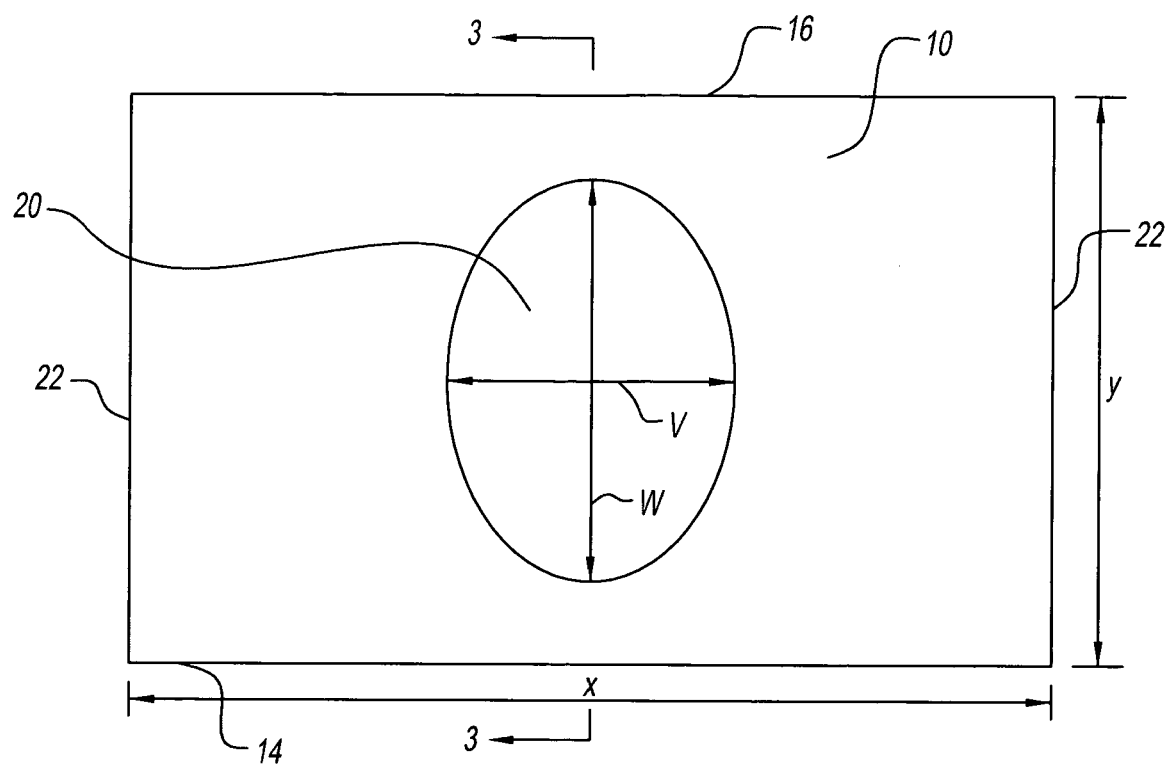
FIG. 1 is a plan view of the anti-snoring pillow of an exemplary embodiment of the invention showing the overall dimensions and location of the oval concavity.
Figure 2:
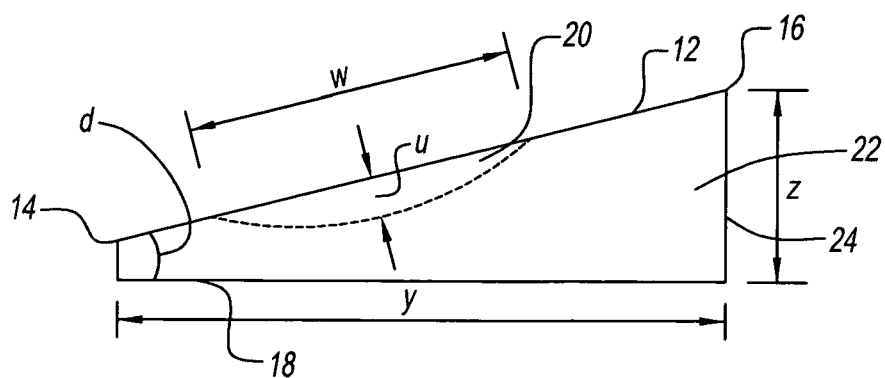
FIG. 2 is a side elevation view of FIG. 1 showing the dimensional relationships and the angle of inclination of the top of the pillow relative to the horizontal plane.
Figure 3:
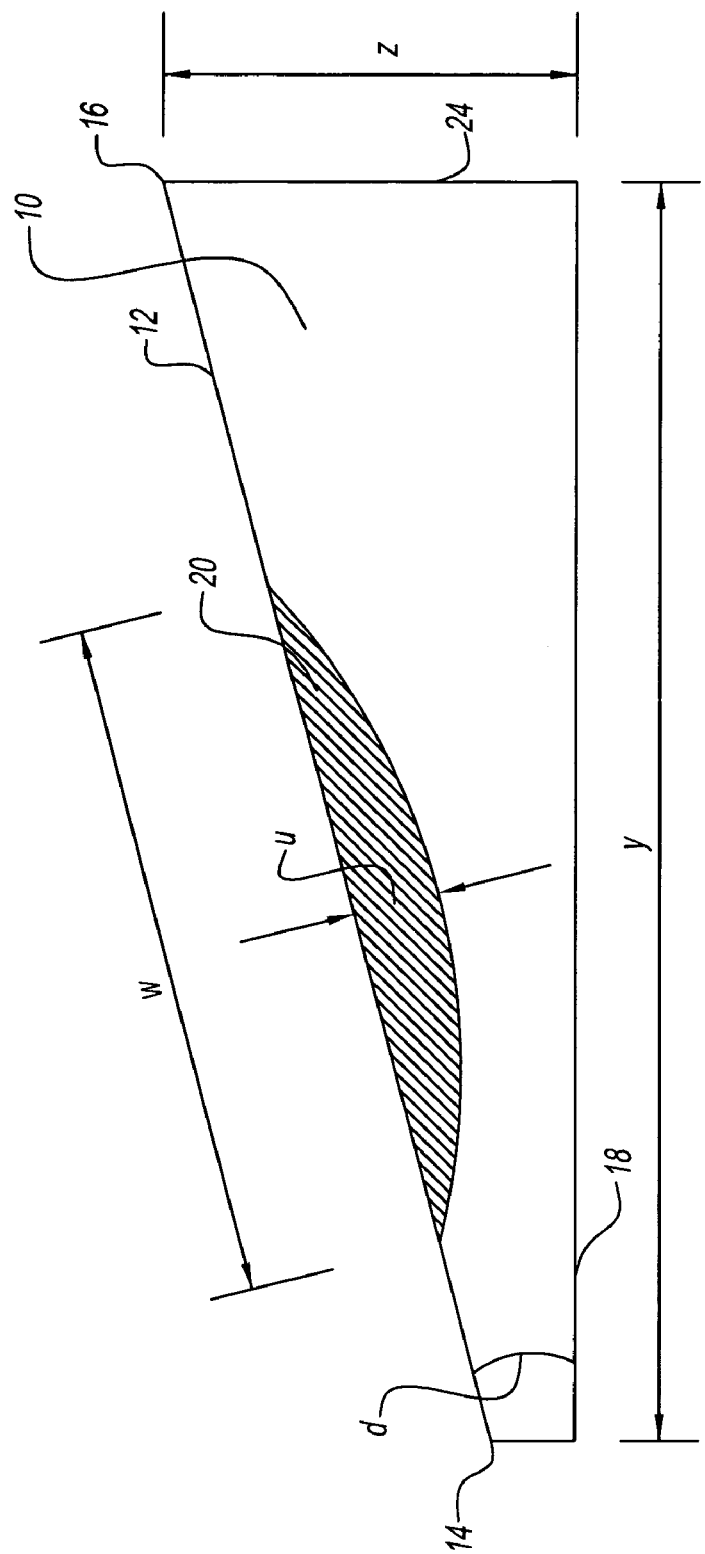
FIG. 3 is a cross-section "3—3" of FIG. 1 showing the relative dimensions of the oval concavity.

With reference to FIGS. 1–3, which illustrate various aspects of one specific embodiment of the anti-snoring pillow of the invention, shown are the generally wedge shaped section 10, having a length x, a width y, a top surface 12, a front edge 14 of the top surface 12, a back edge 16 of the top surface 12, and a bottom surface 18. Top surface 12 forms an angle d with the plane of bottom surface 18.

The top surface 12 of the generally wedge shaped section 10 is provided with a generally oval shaped concavity 20, which is located in a central position relative to either side 22 of the generally wedge shaped section 10.

Concavity 20 has an overall dimension from top to bottom w and an overall dimension from side to side v, of sufficient size to comfortably accommodate a human head. Concavity 20 has a maximum depth u at the deepest point thereof, measured from the plane of top surface 12.

Figure 4:
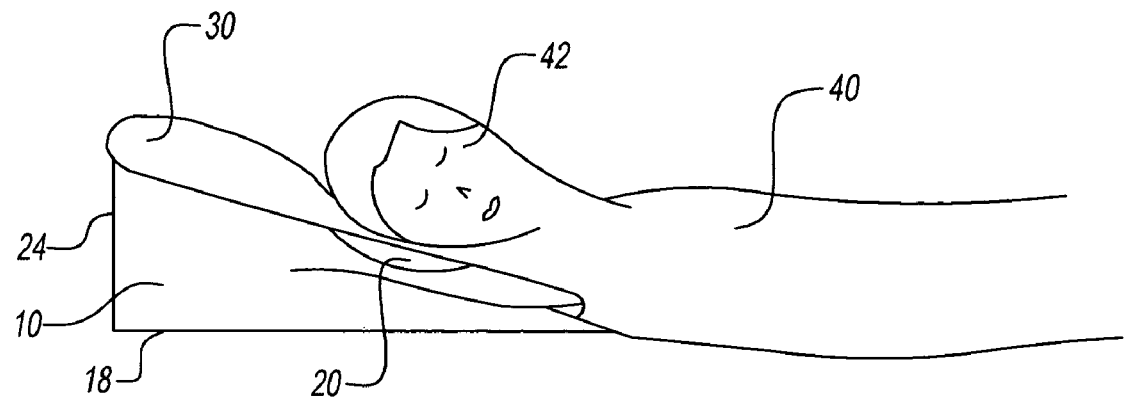
FIG. 4 is a side elevation view of the pillow of FIG. 1 showing the use of the pillow of FIG. 1 together with a conventional soft density bed pillow with the user in a sleeping position.

With reference to FIG. 4, which illustrates a side elevation view of the anti-snoring pillow of the invention together with a conventional soft density bed pillow with the user in a sleeping position, shown is the generally wedge shaped section 10, the soft density bed pillow 30, and the user 40. The users head 42 is positioned on the soft density bed pillow 30, which is in turn partially nestled into concavity 20 where the user's head 42 rests on a wedge shaped section 10, which lies on its bottom surface 18.

Figure 5:
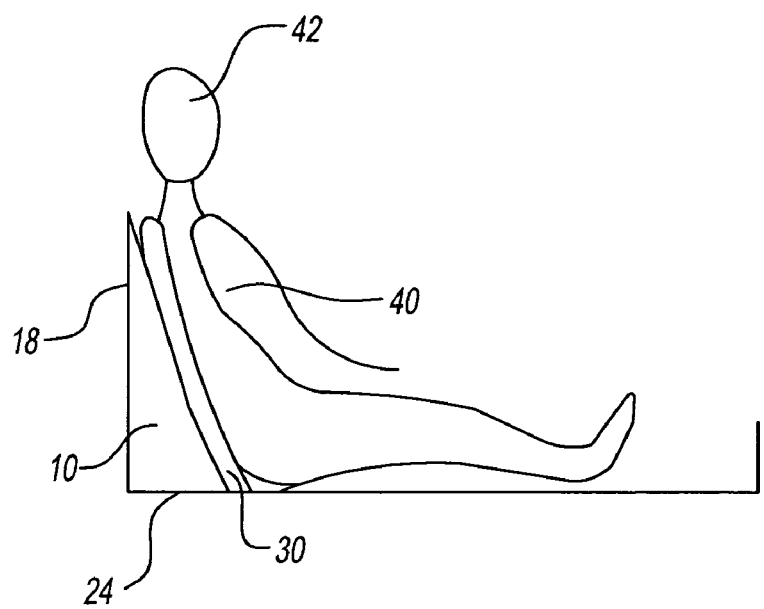
FIG. 5 is a side elevation view of the pillow anti-snoring pillow of the invention showing the use of the pillow of FIG. 1 together with a conventional soft density bed pillow, with the user in a sitting position, and the anti-snoring pillow used as a backrest.

With reference to FIG. 5, which illustrates a side elevation view of the anti-snoring pillow of the invention together with a conventional soft density bed pillow with the user in a sitting position and the anti-snoring pillow used as a backrest, shown is the generally wedge shaped section 10, the soft density bed pillow 30, and the user 40 in a sitting position. Wedge shaped section 10, rests on back surface 24, with bottom surface 18 now forming the back of the wedge shaped section 10.

Generally speaking, it is contemplated that the overall length x of the generally wedge shaped section 10, will be between 16 inches and 36 inches, and preferably will be about 18 inches. The overall width of the generally wedge shaped section 10 will be from about 10 inches to about 24 inches and preferably will be about 14 inches. It is contemplated that angle d be from about 5 degrees to about 20 degrees, and preferably will be from about 10 degrees to about 15 degrees, in order for the generally wedge shaped section 10 to effectively function as an anti-snoring pillow.

It is also contemplated that concavity 20 will have dimensions v and w, which approximate those of the human head. That is to say, dimension v will be from about 8 inches to about 11 inches, and preferably will be from about 9 inches to about 10 inches; and dimension w will be from about 8 inches to about 12 inches and preferably will be from about 9 inches to about 10 inches. The depth u of concavity 20 will generally be from about 1 inch to about 2 inches, and preferably will be about 1¼ inches to about 1¾ inches.

Most preferably, dimension v of concavity 20 will be about 9 inches, dimension w of concavity 20 will be about 9 inches, and dimension u of concavity 20 will be about 1½ inches.

It is preferred that generally wedge shaped section 10 be composed of a minimally resilient material in order to achieve the necessary support to the user to achieve the effect of reduction or elimination of snoring in a sleeping individual. It is contemplated that the most practical materials of construction for wedge shaped section 10 will be a semi-rigid foam material such as would provide the necessary degree of support required. The specific nature of the material utilized is not critical so long as it is non-irritating to the human user and is capable of being shaped into the size and shape required, in such a manner as would provide the necessary support to the user, so as to properly position the user's head to eliminate snoring.

It is contemplated that the most practical material of construction for wedge shaped section 10 will be a medium density polyurethane type foam which is rigid enough to meet the aforementioned criteria.

It will be apparent to one skilled in this art that variations in the type and density of the foam material which may be utilized in constructing the wedge shaped section 10 will be required in order to provide the most beneficial results for a given individual, depending upon that individual's size and weight, as well as that individual's overall degree of musculature around the neck and head.

Moreover, it is also contemplated that the anti-snoring pillow of the invention may optionally include a fitted or non-fitted covering comprised of a variety of commonly used fabrics, which have conventionally been employed as pillow coverings. Such fitted or non-fitted covering may be attached to the anti-snoring pillow of the invention using any number of conventional means such as, for example, zipper closures, buttons, snaps and hook-and-loop type closures.

Figure 6:
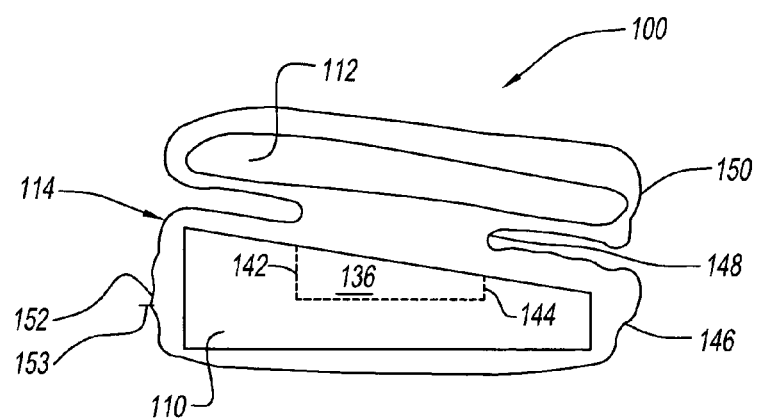
FIG. 6 is a side view of an alternate exemplary embodiment of an anti-snoring pillow.

Referring now to FIG. 6, an alternate embodiment of an anti-snoring pillow according to the present invention is generally represented by reference number 100 having an exemplary embodiment of the aforementioned covering. Anti-snoring pillow 100 includes bottom pillow 110 and a top pillow 112 disposed in a covering 114.

Figure 7:
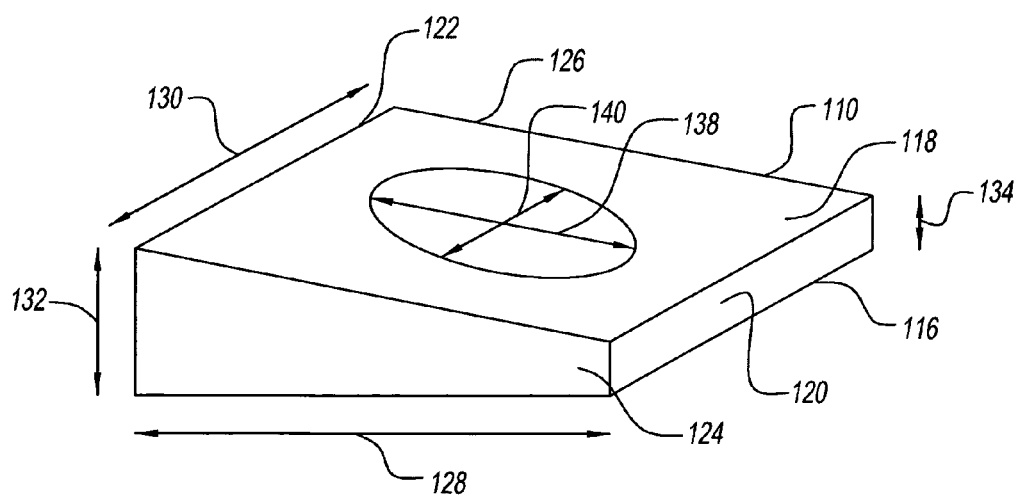
FIG. 7 is a side perspective view of the wedge shaped section of FIG. 6.

Bottom pillow 110, illustrated in FIGS. 6 and 7, has four generally planar surfaces and two generally planar side surfaces defining a substantially wedge shape. Bottom pillow 110 has a bottom surface 116, a top surface 118, a front surface 120, a rear surface 122, a first side 124, and a second opposite side 126. Top surface 118 is angled with respect to bottom surface 120 from about five degrees to about twenty degrees, and preferably will be from about ten degrees to about fifteen degrees, most preferably about twelve degrees.

In an exemplary embodiment, bottom pillow 110 has a depth 128 of about fourteen inches and a width 130 of about eighteen inches. In this embodiment, rear surface 122 has a height 132 of about four and a half inches, while front surface 120 has a height 134 of about two inches.

Top surface 118 has a head-receiving cavity 136 defined therein. Preferably, cavity 136 has overall dimensions of sufficient size to comfortably accommodate a human head when in a first sleeping position (FIG. 8) and a second sleeping position (FIG. 9). In an exemplary embodiment, cavity 136 is ovoid in shape and has a length 138 of about eleven inches and a width 140 of about 10 inches. In this embodiment, cavity 136 has a first depth 142 proximate rear surface 122 of about one and a half inches and a second depth 144 proximate front surface 120 of about one inch. First and second depths 142, 144 are measured from top surface 118 to the bottom of cavity 136.

It should be recognized that cavity 136 is described above by way of example as ovoid. Of course, it is contemplated by the present invention for cavity 136 to any desired shape that comfortably accommodates a human head when in a first sleeping position (FIG. 8) and a second sleeping position (FIG. 9).

Cavity 136 is, preferably, located in a central position within top surface 118. For example, cavity 136 can be centrally located in top surface 118 relative to surfaces 120, 122, 124, and 126.

Bottom pillow 110 can be formed of a medium density polyurethane type foam that is rigid enough to meet the aforementioned criteria. In an exemplary embodiment, bottom pillow 110 can have a density of about 1.2 pounds per cubic foot and an indentation force deflection (herein after "IFD") between about 30 to about 38 at twenty-five percent deflection at four inches thick. By way of comparison, the aforementioned IFD is approximately equal to that commonly found in firm mattresses. For example, bottom pillow 110 can be 1235 CM grade polyurethane foam commercially available from Leggett & Platt.

It has been found that bottom pillow 110 having cavity 136 is sufficient to position and support the user to achieve the effect of reduction and/or elimination of snoring during sleep.

Top pillow 112 is formed of a material that is, preferably, softer and less dense than bottom pillow 110 so that the top pillow can enhance the comfort of the bottom pillow. However, top pillow 112 has a density and thickness that allows the top pillow to deform such that the user's head rests in cavity 136 of bottom pillow 110 during use. In this manner, top pillow 112 does not interfere with the anti-snoring effects of bottom pillow 110.

In an exemplary embodiment, top pillow 112 can have an IFD between about six to about 12 at twenty-five percent deflection at four inches thick. By way of comparison, the aforementioned IFD is approximately equal to that commonly found in common bed pillows.

In one exemplary embodiment, top pillow 112 is formed of a polyester or a polyester fill material having an IFD of about nine and a thickness of about two inches. While top pillow 112 is described above by way of example as polyester fill, it is also contemplated by the present invention for top pillow 112 to be formed of other man-made materials, as well as natural materials (e.g., down feathers), and or combinations thereof.

Covering 114 includes a bottom section 146, a middle section 148, and a top section 150. Bottom section 146 can receive bottom pillow 110, while top section 150 can receive top pillow 112.

Advantageously, it has been found that middle section 148 of covering 114 aids in maintaining top pillow 112 properly positioned with respect to cavity 136. For example, middle section 148 maintains top pillow 112 centered over cavity 136 during use of anti-snoring pillow 100. In an exemplary embodiment, middle section 148 is sized substantially equal to the dimensions of cavity 136 (i.e. length 138 and width 140) and is positioned over the cavity. Since middle section 148 is over cavity 136 and substantially equal in size with respect to the cavity, covering 114 maintains top pillow 112 properly positioned over the cavity.

Middle section 148 can be provided by way of pleats or seams in covering 114. Of course, other methods of providing covering 114 with middle section 148 are contemplated by the present invention.

It has also been found that covering 114 provides the added benefit of giving top pillow 112 the feel and utility of a normal bed pillow. For example, normal bed pillows can be fluffed up from their bottom surface. Advantageously, middle section 148 aids in separating top pillow 112 from bottom pillow 110, which allows the user to fluff the top pillow as would commonly be done with normal bed pillows.

Covering 114 can be a fitted or non-fitted fabric covering made of man-made fibers, natural fibers, or any combinations thereof. For example, covering 114 can be made of fabrics commonly used as bed pillow cases.

In some embodiments, bottom pillow 110 and/or top pillow 112 can be selectively removable from covering 114. For example, covering 114 can include one or more openings 152 (only one shown). In other embodiments, openings 152 can be secured in a closed position using any number of conventional closing means 153 such as, for example, a zipper closure, a button closure, a snap closure, a hook-and-loop type closure, or any combinations thereof.

Figure 8:
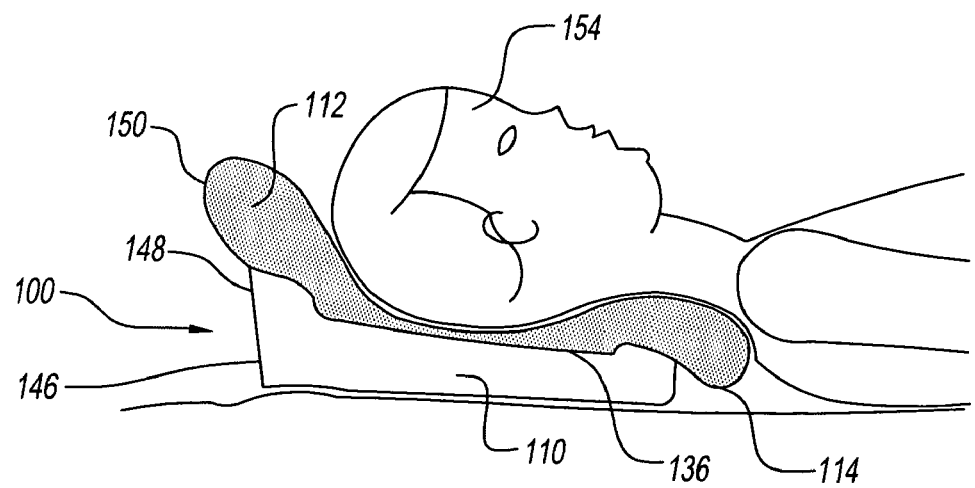
FIG. 8 is a side elevation view of the anti-snoring pillow of FIG. 6 in use in a first sleeping position.
Figure 9:
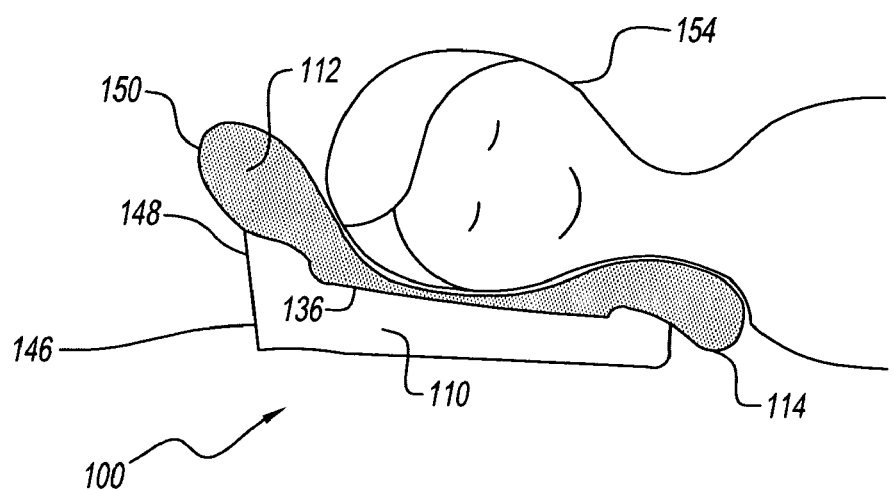
FIG. 9 is a side elevation view of the anti-snoring pillow of FIG. 6 in use in a second sleeping position.

Referring now to FIGS. 8 and 9, anti-snoring pillow 100 finds equal use when sleeping on one's side or back. In use, the head 154 of the user is positioned in the middle of top section 150 and, thus, on top pillow 112. Since covering 114 maintains top pillow 112 over cavity 136, head 154 deforms the top pillow into the cavity.

It should be recognized that anti-snoring pillow 100 having covering 114 is described by way of example only having bottom pillow 110 and top pillow 112 as described in FIGS. 6 and 7. Of course, it is contemplated by the present invention for bottom pillow 110 to be as described above with respect to FIGS. 1–3 and/or for top pillow 112 to be as described above with respect to FIGS. 4–5.

It should also be noted that the terms "first", "second", "third", "upper", "lower", and the like may be used herein to modify various elements. These modifiers do not imply a spatial, sequential, or hierarchical order to the modified elements unless specifically stated.

While the present invention has been described with reference to one or more exemplary embodiments, it will be understood by those skilled in the art that various changes may be made and equivalents may be substituted for elements thereof without departing from the scope of the present invention. In addition, many modifications may be made to adapt a particular situation or material to the teachings of the invention without departing from the scope thereof. Therefore, it is intended that the present invention not be limited to the particular embodiment(s) disclosed as the best mode contemplated, but that the invention will include all embodiments falling within the scope of the appended claims.

What is claimed is:

1. An anti-snoring pillow comprising:
   a top pillow having a first density;
   a bottom pillow having a second density, said second density being higher than said first density, said bottom pillow having a top surface angled with respect to a bottom surface of said bottom pillow, said top surface of said bottom pillow having a head-receiving cavity defined therein; and
   a covering having a top section, a middle section, and a bottom section, said top pillow being received in said top section and said bottom pillow being received in said bottom section, said top section surrounding said top pillow with a top portion of the top section covering a top surface of the top pillow and a bottom portion of the top section at least partially covering a bottom surface of the top pillow, said bottom section surrounding said bottom pillow with a top portion of the bottom section at least partially covering said top surface of said bottom pillow and a bottom portion of said bottom section covering said bottom surface of said bottom pillow, said middle section being smaller than said bottom section and said top section, said middle section extending between said bottom surface of said top pillow and said top surface of said bottom pillow with said middle section having sides and ends substantially equal to a length and a width, respectively, of said head-receiving cavity to form an area substantially equal to said head-receiving cavity to thus maintain said top pillow over said head-receiving cavity during use, wherein said top surface has an angle of about 5 degrees to about 20 degrees with respect to said bottom surface of said bottom pillow.

2. The anti-snoring pillow as in claim 1, wherein said bottom pillow has a front surface having a height of about 2 inches.

3. The anti-snoring pillow as in claim 1, further comprising one or more openings defined in said covering for selectively removing said bottom pillow and/or said top pillow from said covering.

4. The anti-snoring pillow as in claim 3, further comprising means for selectively closing said one or more openings.

5. The anti-snoring pillow as in claim 1, wherein said top pillow, said bottom pillow, and said covering are formed of a material selected from the group consisting of man-made material, natural material, and any combinations thereof.

* * * * *